United States Patent [19]

Frankenreiter

[11] Patent Number: 4,984,577
[45] Date of Patent: Jan. 15, 1991

[54] OSCILLOMETRIC NON-INVASIVE METHOD FOR MEASURING BLOOD PRESSURE AND APPARATUS FOR AUTOMATED OSCILLOMETRIC BLOOD PRESSURE MEASURING

[75] Inventor: Michael Frankenreiter, Sindelfringen, Fed. Rep. of Germany

[73] Assignee: Hewlett-Packard Company, Palo Alto, Calif.

[21] Appl. No.: 326,147

[22] Filed: Mar. 20, 1989

[51] Int. Cl.$^5$ .............................................. A61B 5/02
[52] U.S. Cl. .................................... 128/681; 128/682; 128/683
[58] Field of Search ......................... 128/672, 677–686

[56] References Cited

U.S. PATENT DOCUMENTS 4,427,013  1/1984  Nunn et al. ...................... 128/681

FOREIGN PATENT DOCUMENTS 0249243  6/1987  European Pat. Off. .
8803003  9/1987  PCT Int'l Appl. .

Primary Examiner—Max Hindenburg
Assistant Examiner—J. P. Lacyk

[57] ABSTRACT

A method and an apparatus for automatic oscillometric blood pressure measuring determines a sequence of peak amplitudes. Two points $p_{e1}$, $p_{e2}$ are evaluated on an envelope (10) of said peak sequence, said points $p_{e1}$, $p_{e2}$ are the base for determining blood pressure values such as mean, diastolic and systolic pressures.

12 Claims, 2 Drawing Sheets

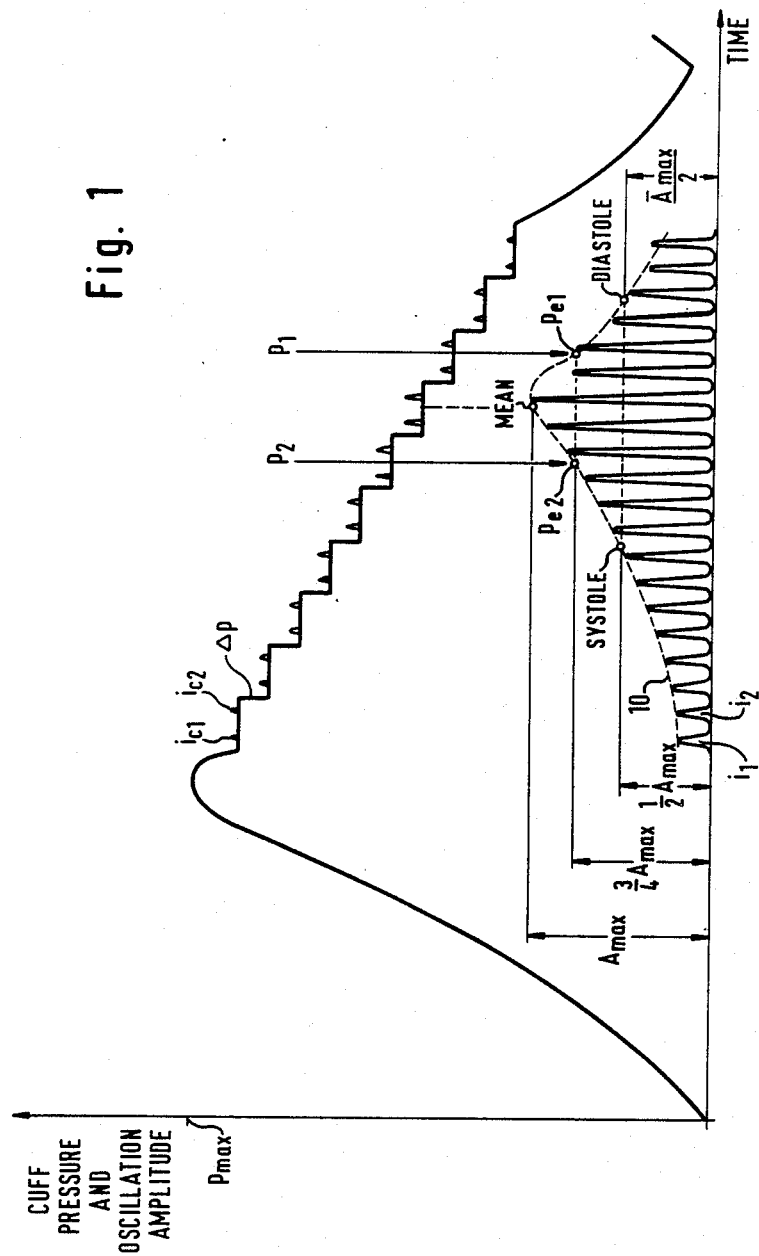

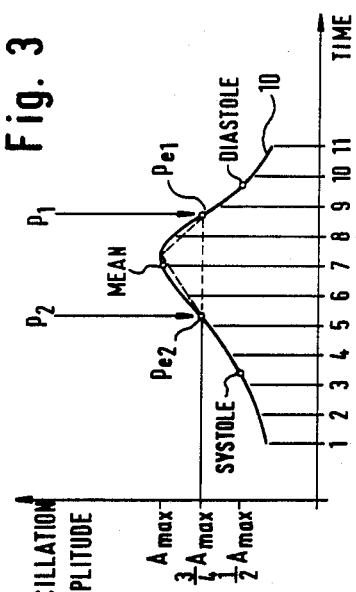
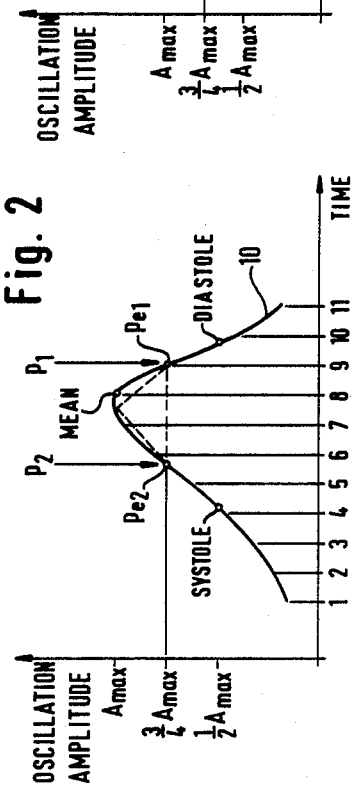
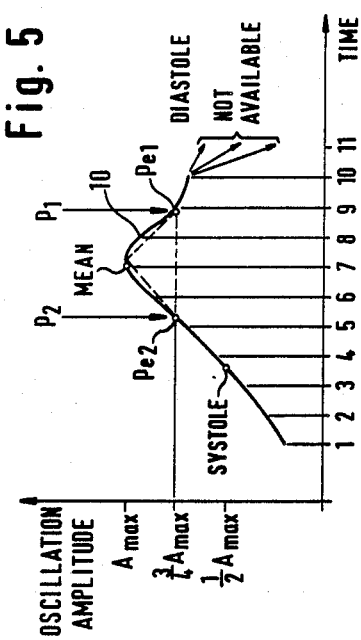
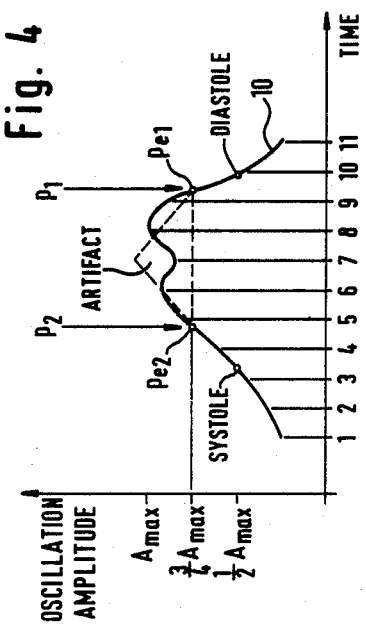

OSCILLOMETRIC NON-INVASIVE METHOD FOR MEASURING BLOOD PRESSURE AND APPARATUS FOR AUTOMATED OSCILLOMETRIC BLOOD PRESSURE MEASURING

BACKGROUND OF THE INVENTION

The present invention relates to an oscillometric noninvasive method and apparatus for measuring blood pressure values and, more particularly, for determining mean, systolic, and diastolic arterial pressures.

The oscillometric method for measuring blood pressure is one of the most popular methods in commercially available systems. This method relies on measuring changes in arterial counterpressure, such as imposed by the inflatable cuff which is controllably relaxed or inflated. The cuff pressure is reduced in predetermined increments, and at each pressure level, fluctuations are monitored. The resulting signals typically consist of the DC voltage with a small superimposed variational component caused by arterial blood pressure pulsations. After suitable filtering to reject the DC voltage component and to provide amplification, peak pulse amplitudes above a given base line are measured and stored. As deflating of the cuff continues, the peak amplitudes will normally increase from a lower level to a relative maximum, and thereafter will decrease. The lowest cuff pressure at which the oscillation has a maximum value is representative of mean arterial pressure. Systolic and diastolic pressures can be derived as a predetermined fraction of mean arterial pressure, or by more sophisticated methods of direct processing of the oscillatory complexes.

One problem of such well-known oscillometric methods and apparatus is that in fact the mean pressure is not disposed exactly at the maximum peak amplitude. Another problem is that neither the systolic nor the diastolic pressures are disposed exactly at an oscillation amplitude. Therefore, the systolic, mean and diastolic values are inaccurate and differ up to a half size of a deflation step.

A further problem is in determining the mean if artifacts are recognized; said artifacts may cause an incorrect array of peak amplitudes in the area of the mean. For example, artifacts may be caused by movements of the subject during measuring. The transition from the increasing branch of an envelope of the peak amplitude sequence to the decreasing branch of said envelope is, therefore, not smooth. For example, sometimes in the transition are of increasing and decreasing branches two amplitudes of high intensity are obtained, having a less intensive amplitude therebetween. The resulting wave-shaped envelope in the mean area does not allow a determination of the mean.

Artifacts in the area of the systolic and diostolic values may be compensated by interpolation as described within EP-A2-0 207 806 and EP-A2 0 207 807. However, based on the fact that the contact between the cuff and the limb of the subject is not strong during the diastolic pressure interval, such artifacts may cause the peak amplitudes within the diastolic pressure area at the decreasing branch of the envelope to be incorrect or not obtainable.

It is, therefore, an object of the present invention to provide a method and an apparatus for oscillometric blood pressure measurings enabling the determination of mean, diastolic and/or systolic pressure values, even though artifacts occur.

SUMMARY OF THE INVENTION

According to the present invention, a method for determining mean, diastolic, and/or systolic pressures comprises the steps of applying a blood pressure cuff about a subject's limb containing an artery, inflating said cuff to a pressure above the systolic pressure, thereby occluding said artery, reducing cuff pressure step by step, thereby permitting an increasing flow through the progressively less occluded artery, monitoring arterial counterpressure oscillations at each cuff pressure reducing step, converting said oscillations into voltage signals, processing said voltage signal oscillations into a sequence of peak amplitudes covered by an envelope, evaluating at least two points of said envelope, a first point $p_{e1}$ disposed within an area of the decreasing branch of said envelope, said area corresponding to a situation wherein the contact between cuff and limb of the subject is sufficiently strong for obtaining correct peak amplitudes, a second point $p_{e2}$ disposed on the incresing branch of said envelope, determining cuff pressure values $p_1$ and $p_2$ corresponding to $p_{e1}$ and $p_{e2}$, respectively and determining systolic mean, and diastolic pressure using said cuff pressure values $p_1$ and $p_2$.

The present invention provides an apparatus for automated oscillometric blood pressure measuring, comprising an inflatable and deflatable cuff, means for inflating said cuff and for deflating said cuff step by step, monitoring means for monitoring arterial counterpressure oscillations at each cuff pressure reducing step, pressure transducer means coupled to said cuff for converting said oscillations to voltage signals, processing means for processing said complex voltage signal oscillations into a sequence of peak amplitudes enveloped by an envelope, evaluating means for evaluating at least two points of said envelope, a first point $p_{e1}$ disposed within an area of the decreasing branch of said envelope, said area corresponding to situations wherein the contact between cuff and limb of the subject is sufficiently strong for obtaining correct peak amplitudes, a second point $p_{e2}$ disposed on the increasing branch of said envelope, processing means for determining cuff pressure values $p_1$ and $p_2$ corresponding to $p_{e1}$ and $p_{e2}$, respectively said processing means further determining systolic, mean, and diastolic pressures, thereby using said cuff pressure values $p_1$ and $p_2$. The evaluation of $p_{e1}$ at the decreasing branch occurs in such a manner that the peak amplitudes supporting the envelope in that area are independent of artifacts in the area of both the mean and the diastolic pressures. Since the contact between pressure cuff and subject's limb is still sufficiently strong, the obtained peak amplitudes and the resulting envelope correspond to the actual values of subject. The evaluation of point $p_{e2}$ at the increasing branch, for example between systole and mean, uses an area of the envelope which are supported by peak amplitudes being independent of artifacts in the mean area. The contact between pressure cuff and subject's limb in this area is excellent, therefore artifacts due to movements of the subject will not cause incorrect peak amplitudes. A line between $p_{e1}$ and $p_{e2}$ will cut the top of the envelope, and the cut area may be replaced by simple geometric graphs such as triangles or more sophisticated graphs, approximating the top of the envelope.

According to another aspect of the invention, said first and second points, $p_{e1}$ and $p_{e2}$, are evaluated at the same level of the envelope. This has the advantage that a simple triangular approximation can be achieved for determining mean, diastolic, and systolic pressures.

According to another aspect of the invention, the mean is determined by approximating the envelope between $p_{e1}$ and $p_{e2}$ to a triangle according to the following equation $$\text{mean pressure} = p_1 + \tfrac{1}{3}(p_2 - p_1).$$

This has the advantage that a simple arithmetic function is sufficient to determine mean pressure.

According to another aspect of the invention, the diastolic and systolic pressures are determined according to the following equations $$\text{systolic pressure} = p_2 + \tfrac{1}{3}(p_2 - p_1),$$

$$\text{diastolic pressure} = p_1 - 1/6(p_2 - p_1).$$

BRIEF DESCRIPTION OF THE DRAWINGS

FIG. 1 shows two superimposed graphs of cuff pressure versus time, and oscillation amplitudes versus time, respectively, demonstrating the present invention.

FIG. 2 shows a graph of oscillation amplitude versus time, demonstrating a second embodiment according to the invention.

FIG. 3 shows a graph similar to as FIG. 2, demonstrating a third embodiment according to the invention.

FIG. 4 shows a graph similar to FIGS. 2 and 3, demonstrating a fourth embodiment of the invention.

FIG. 5 shows a graph similar to FIGS. 2 through 4, demonstrating a fifth embodiment according to the invention.

DESCRIPTION OF THE PREFERRED EMBODIMENTS

Referring now to FIG. 1, the upper graph illustrates a typical cuff pressure/time graph of an oscillometric method of measuring blood pressure.

The cuff is inflated to a pressure $p_{max}$ above the systolic pressure $p_{sys}$, thereby occluding an artery. The cuff pressure is thereupon reduced in predetermined increments $\Delta p$, and at each pressure level fluctuations are monitored. Each step (time interval) is made sufficiently long to include at least two heart beats. Accordingly, at least two cuff pressure comlex pulses $i_{c1}$, $i_{c2}$ (upper graph) are measured during each interval after such pulses begin. After suitable filtering and amplification, corresponding oscillation peaks $i_1$, $i_2$ (lower graph) are obtained and stored. As deflating of the cuff continues, the oscillation peak amplitudes will normally increase from a lower level to a relative maximum and, thereafter, will decrease (see in particular the lower graph in FIG. 1). The lowest cuff pressure at which the amplitude has a maximum value $A_{max}$ is normally representative of mean arterial pressure. However, by constructing an envelope 10, enveloping the array of peak amplitudes, it can be determined that the mean pressure 10 is not always identical with the maximum peak amplitude $A_{max}$ at the top of envelope 10.

Furthermore, neither the systolic pressure nor the diastolic pressure, indicated by the points labeled systole and diastole, respectively, in the figures, corresponds exactly to a measured peak amplitude. Systole and diastole are located at approximately linear sections of the envelope 10, therefore systole and diastole may be determined by linear interpolation of two adjacent peak amplitudes.

However, the peak amplitudes in the decreasing branch of the envelope 10 about the diastole are sometimes difficult to determine when the contact is not strong between the cuff and the subject's limb, for example an upper arm of a human. Therefore, artifacts caused by a movement of said upper arm will result in a non-linear course of the envelope 10 within said diastole area. The envelope 10 of FIG. 1 represents a more ideal course, but in practice the envelopes are more irregular, for example as demonstrated within FIGS. 2 through 5.

Turning now to FIGS. 2 through 5, there are shown oscillation amplitude/time graphs corresponding to oscillometric methods of measuring blood pressure. Within each diagram, eleven peak amplitudes are shown, each amplitude being representative of the arithmetic mean of two peak amplitudes within one deflating step.

As can be seen from FIGS. 2 and 3, the maximum amplitude $A_{max}$ does not correspond to the top of the envelope 10.

Within FIG. 4, peak amplitude no. 7 is of lower intensity than adjacent peak amplitudes nos. 6 and 8. If evaluating peak amplitude no. 8 as mean, the corresponding mean blood pressure deviates considerably from the actual mean blood pressure of subject, which actual mean is in the range of peak amplitude 7.

Within FIG. 5, the intensity of peak amplitude 10 is too high, and peak amplitude 11 is not available. This is caused by the less intense contact between cuff and limb of the subject measured.

According to the present invention using the envelopes 10, enveloping at least the peak amplitudes nos. 1 through 10, as illustrated in FIGS. 1 through 5, the determination of mean, systolic, and, in particular, diastolic pressures is made by evaluating two points $p_{e1}$ and $p_{e2}$, on the envelopes 10. The ordinates of points $p_{e1}$ and $p_{e2}$ in the Cartesian coordinate system is $0.75 \times A_{max}$. Both points $p_{e1}$ and $p_{e2}$ are located on the envelopes 10 within areas at which the course of said envelopes 10 is approximately linear. Furthermore, points $p_{e1}$ and $p_{e2}$ are apart from the mean of the envelope, therefore independent of artifacts in the mean area.

The point $p_{e1}$ is located on the decreasing branch of the envelopes 10 between mean and diastole. The point $p_{e1}$ is evaluated such that it is apart from the mean but in an area wherein the contact between cuff and subject's limb is still intense. For determining subject's individual blood pressure values, cuff pressure values $p_1$ and $p_2$ corresponding to points $p_{e1}$ and $p_{e2}$, respectively are determined.

Therefore, an apparatus according to the invention determines the envelopes 10 of said oscillation peak sequence, evaluates with evaluating means the two points $p_{e1}$ and $p_{e2}$, and determines with processing means the corresponding cuff pressure values $p_1$ and $p_2$ from stored cuff pressure values.

Based on the postulation that the envelope 10 between points $p_{e1}$ and $p_{e2}$ approximately corresponds to a triangle, the mean pressure value can be determined according to equation 1.

$$\text{Mean pressure} = p_1 + \tfrac{1}{3}(p_2 - p_1) \qquad \text{Eq. 1}$$

Furthermore, the systolic and diastolic pressures can be determined according to the equations 2 and 3.

$$\text{Systolic pressure} = p_2 + \tfrac{1}{2}(p_2 - p_1) \quad \text{Eq. 2}$$

$$\text{Diastolic pressure} = p_1 - 1/6(p_2 - p_1) \quad \text{Eq. 3}$$

Using equations 1 through 3 for determining mean, systolic, and diastolic pressures, excellent results can be obtained up to incremental pressure reducing steps of 2,128 kPa(16 mmHg). In the preferred embodiment as shown in FIGS. 1 through 5, the points $p_{e1}$ and $p_{e2}$ are always evaluated at $\tfrac{3}{4} A_{max}$. However, points $p_{e1}$ and $p_{e2}$ in the range of 0,65 to 0,85 $A_{max}$ give good results. Furthermore, it is not necessary that both points $p_{e1}$ and $p_{e2}$ be at the same level.

Furthermore, it is possible to use more than two points $p_{e1}$ and $p_{e2}$, with at least one point on the increasing and one point on the decreasing branch of the envelope.

Furthermore, if more sophisticated equipment is available, the envelope between points $p_{e1}$ and $p_{e2}$ can be approximated by graphs other than a triangle.

These and other variations upon and modifications to the described embodiments are provided for by the present invention, the scope of which is limited only by the following claims.

I claim:

1. An oscillometric non-invasive method for measuring blood pressure, comprising the steps of:
   (a) applying a blood pressure cuff about a subject's limb containing an artery;
   (b) inflating said cuff to a cuff pressure above the systolic blood pressure of said artery, therby occluding said artery;
   (c) reducing said cuff pressure step by step, thereby permitting an increasing flow through the progressively less occluded artery;
   (d) monitoring arterial counterpressure oscillations at each cuff pressure reducing step;
   (e) converting said counterpressure oscillations to voltage signals;
   (f) processing said voltage signals into a sequence of peak amplitudes enveloped by an envelope;
   (g) evaluating at least two points $p_{e1}$ and $p_{e2}$ on said envelope, the first point $p_{e1}$ disposed within an area of a decreasing branch of said envelope, said area corresponding to situations wherein the contact between said cuff and said limb is sufficiently strong for obtaining correct peak amplitudes, the second point $p_{e2}$ disposed on an increasing branch of said envelope;
   (h) determining at least two cuff pressure values, said pressure values including values $p_1$ and $p_2$ corresponding respectively to said points $p_{e1}$ and $p_{e2}$; and
   (i) determining mean, systolic, and diastolic pressures using said at least cuff pressure values $p_1$ and $p_2$.

2. A method as recited in claim 1 wherein step (g) further comprises evaluating said two points $p_{e1}$ and $p_{e2}$ at the same level of said envelope.

3. A method as recited in claim 2 wherein step (g) further comprises evaluating said two points $p_{e1}$ and $p_{e2}$ on said envelope (10) within the range of 0.65 to 0.85 of the maximum of said sequence of peak amplitudes.

4. A method as recited in claim 2 wherein step (g) further comprises evaluating said two points $p_{e1}$ and $p_{e2}$ on said envelope at $\tfrac{3}{4}$ of the maximum of said sequence of peak amplitudes.

5. A method as recited in claim 2 wherein step (i) further comprises determining said mean pressure by approximating said envelope between $p_{e1}$ and $p_{e2}$ to a triangle according to equation 1, $$\text{mean pressure} = p_1 + \tfrac{1}{2}(p_2 - p_1) \quad \text{Eq. 1}$$

6. A method as recited in claim 1 wherein step (i) further comprises determining said diastolic and systolic pressures according to equations 2 and 3, $$\text{systolic pressure} = p_2 + \tfrac{1}{2}(p_2 - p_1) \quad \text{Eq. 2}$$

$$\text{diastolic pressure} = p_1 - 1/6(p_2 - p_1) \quad \text{Eq. 3}$$

7. An apparatus for automatic oscillometric blood pressure measuring, comprising:
   an inflatable and deflatable cuff;
   controlling means for controlling cuff pressures, so as to inflate said cuff to a maximum cuff pressure and deflate said cuff in predetermined cuff pressure reducing steps;
   monitoring means for monitoring arterial counterpressure oscillations at each of said cuff pressure reducing steps;
   pressure transducer means coupled to said cuff for converting said counterpressure oscillations to voltage signals;
   processing means for processing said voltage signals into a sequence of peak amplitudes, said sequence being enveloped by an envelope;
   evaluating means for evaluating at least two points $p_{e1}$ and $p_{e2}$ on said envelope, the first point $p_{e1}$ disposed within an area of a decreasing branch of said envelope, said area corresponding to situations wherein the contact between said cuff and a limb of said subject is sufficiently strong for obtaining correct peak amplitudes, the second point $p_{e2}$ disposed on an increasing branch of said envelope; and
   determining means for determining cuff pressure values $p_1$ and $p_2$ corresponding to said points $p_{e1}$ and $p_{e2}$, said determining means further determining mean, systolic, and diastolic pressures using said cuff pressure values $p_1$ and $p_2$.

8. An apparatus as recited in claim 7 wherein said evaluating means evaluate said first and second points $p_{e1}$ and $p_{e2}$ at the same level of said envelope.

9. An apparatus as recited in claim 8 wherein said evaluating means evaluate said two points $p_{e1}$ and $p_{e2}$ on said envelope (10) within the range of 0.65 to 0.85 of the maximum of said sequence of peak amplitudes.

10. An apparatus as recited in claim 8 wherein said evaluating means evaluate said two points $p_{e1}$ and $p_{e2}$ on said envelope (10) at $\tfrac{3}{4}$ of the maximum of said sequence of peak amplitudes.

11. An apparatus as recited in claim 8 wherein said determining means determine mean pressure value according to equation 1:

$$\text{mean pressure} = p_1 + \tfrac{1}{2}(p_2 - p_1) \quad \text{Eq. 1}$$

12. An apparatus as recited in claim 8 wherein said determining means determine systolic and diastolic pressures according to equations 2 and 3:

$$\text{systolic pressure} = p_2 + \tfrac{1}{2}(p_2 - p_1) \quad \text{Eq. 2}$$

$$\text{diastolic pressure} = p_1 - 1/6(p_2 - p_1) \quad \text{Eq. 3}$$

* * * * *